United States Patent
Medoff

(12) 
(10) Patent No.: US 8,418,944 B2
(45) Date of Patent: *Apr. 16, 2013

(54) COOLING AND PROCESSING MATERIALS

(75) Inventor: Marshall Medoff, Brookline, MA (US)

(73) Assignee: Xylero, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/859,003

(22) Filed: Aug. 18, 2010

(65) Prior Publication Data

US 2011/0011960 A1  Jan. 20, 2011

Related U.S. Application Data

(63) Continuation of application No. 12/502,629, filed on Jul. 14, 2009, now Pat. No. 7,900,857.

(60) Provisional application No. 61/081,709, filed on Jul. 17, 2008.

(51) Int. Cl.
*B02C 19/00* (2006.01)

(52) U.S. Cl.
USPC .................................. 241/23; 241/25

(58) Field of Classification Search .......... 241/23, 241/65, 25, 101.2
See application file for complete search history.

(56) References Cited

U.S. PATENT DOCUMENTS

| | | | |
|---|---|---|---|
| 4,044,198 A * | 8/1977 | Kostrzewa et al. | 536/86 |
| 4,609,624 A * | 9/1986 | Rothlisberger | 435/157 |
| 4,776,173 A * | 10/1988 | Kamarei et al. | 62/63 |
| 5,372,939 A * | 12/1994 | Lastick et al. | 435/165 |
| 5,431,348 A * | 7/1995 | Orsolini et al. | 241/23 |
| 6,251,643 B1 * | 6/2001 | Hansen et al. | 435/163 |
| 7,678,931 B2 * | 3/2010 | Fichtali et al. | 554/20 |
| 2008/0020437 A1 * | 1/2008 | Savarese | 435/165 |
| 2008/0311639 A1 * | 12/2008 | Navapanich et al. | 435/165 |
| 2009/0093028 A1 * | 4/2009 | Peterson et al. | 435/105 |
| 2010/0330648 A1 * | 12/2010 | Harvey et al. | 435/209 |

* cited by examiner

*Primary Examiner* — Mark Rosenbaum

(57) ABSTRACT

Systems and methods for cooling and processing materials are disclosed.

15 Claims, 2 Drawing Sheets

COOLING AND PROCESSING MATERIALS

RELATED APPLICATIONS

This application is a continuation of U.S. Ser. No. 12/502,629, filed Jul. 14, 2009, now U.S. Pat. No. 7,900,857, which claims benefit of U.S. Provisional App. No. 61/081,709, filed Jul. 17, 2008. The entire contents of the above applications are incorporated by reference herein.

BACKGROUND

Biomass, particularly biomass waste, is abundantly available. It would be useful to derive materials and fuel, such as ethanol, from biomass.

It would also be useful to more efficiently process petroleum containing materials to obtain fuels and other products.

SUMMARY

Materials, such as biomass and other materials, such as petroleum products, can be processed to alter their structures at one or more levels by cooling and processing. The processed materials can then be used, e.g., as sources of further materials and fuel.

Many embodiments of this application use Natural Force™ chemistry. Natural Force™ chemistry methods use the controlled application and manipulation of physical forces, such as particle beams, gravity, light, temperature, etc., to create intended structural and chemical molecular change.

Lignin present in many different types of biomass, including cellulosic and lignocellulosic biomass, can complicate efforts to alter the biomass to form intermediate feedstock for conversion to simpler sugars and, ultimately, products such as alcohols. As a result, yields of products, such as ethanol obtained from biomass, can be less (and in some cases, considerably less) than maximum theoretical yields of such products.

The methods disclosed herein utilize cooling and processing of materials, e.g., cryogenic cooling, alone or in combination one or more with other processing techniques, such as one or more processing steps that may include, e.g., grinding, milling, agitating, abrading, chopping, shearing, water knifing, gas knifing, steam knifing, one or more radiation processing steps (e.g., exposure to charged particles such as electrons and/or ions), one or more sonication processing steps, one or more chemical processing steps (e.g., using agents such as acids, bases, oxidizing agents, reducing agents, and/or solvents), and/or one or more thermal processing steps (e.g., pyrolysis, in the presence of oxidizing and/or other agents, and/or in reduced pressure environments). These other processing techniques, if used, can be performed before, during or after cooling.

By cooling the biomass or other material, the brittleness of various components of the biomass or other material (e.g., hemicellulose and/or lignin and/or proteins and/or pectin and/or minerals) can be increased, thereby significantly improving the effectiveness of the processing techniques that are used to alter the material. By increasing the brittleness of the materials, the materials can be fractured (e.g., the edges of fibers can be fractured) or cracked as a result of various processing steps. Fracturing can be, e.g., microfracturing.

In addition, cooling the material can have other effects that arise from differential rates of expansion and/or contraction of various components of the material. For example, certain components (e.g., lignin with water present) can contract or expand at faster rates than, or in different amounts than other components (e.g., hemicellulose, cellulose) with which they are associated. As a result, the subject material can be weakened, promoting separation (e.g., phase separation, delamination, interfacial cleavage, cracking, or fracturing, e.g., microfracturing) of its various components. These processes—which can occur independently of other processing techniques or in conjunction with other processing techniques—can also improve yields of products, e.g., ethanol obtained from hemicellulose or cellulose that has been separated from lignin. Separation of the lignin from the material reduces the recalcitrance of the material, facilitating conversion of the cellulosic components of the material into a sugar solution (saccharification of the cellulose by an enzyme). Without wishing to be bound by theory, it is believed that the fracturing of the material can allow the enzyme to penetrate the material at the fracture sites, thereby accelerating saccharification. The saccharified material can then be converted to a product, e.g., fermented to ethanol.

When cooling is combined with other processing techniques, e.g., radiation and/or oxidation, the other techniques can be used to a lesser extent to obtain equivalent results. For example, when cooling is used with radiation the radiation can be used at a lower dose to provide the same degree of reduction in recalcitrance.

During the various processing techniques that are used to alter and/or convert materials into other materials, a significant amount of heat can be generated in the materials. To avoid combusting or otherwise initiating unwanted thermal alteration of the materials, the cooling methods disclosed herein can be used to dissipate or offset the excess heat. The extent of cooling (e.g., the amount of heat removed from the material) can be varied according to the amount of heat generated during processing of the material. The extent of cooling can also be adjusted to adjust certain properties of the biomass material, such as its brittleness, to improve the efficiency of certain subsequent processing steps. For example, communution of the hemicellulose, cellulose, and lignin, and separation of these components can be enhanced by the methods disclosed herein.

The cooling and processing methods can also be used to treat other types of materials such as hydrocarbon-containing materials (e.g., petroleum-containing material). Various types of petroleum-containing materials—including heavy and light crude oils, natural gas, oil sands, oil shale, tar sands, bitumen, coal, and/or various hydrocarbon blends—can be cooled and processed using the methods disclosed herein to promote extraction, cracking, communution, separation, and refining of various components of the material, and to regulate temperature during refining, conversion, and purification processes such as cracking, reformation (catalytic and non-catalytic), distillation, and catalytic conversion.

As used herein, a "cryogenic" material is a material at a temperature of 200 K or less (e.g., 170 K or less, 150 K or less, 130 K or less, 120 K or less, 110 K or less, 100 K or less, 90 K or less, 80 K or less, 70 K or less, 60 K or less, 50 K or less, 40 K or less, 30 K or less). Thus, for example, a "cryogenic liquid" is a liquid having a temperature of 200 K or less.

As will be discussed in further detail below, various materials can be used for cooling, including for example liquid nitrogen, carbon dioxide, and ice.

The methods disclosed herein can produce material particles (e.g., fibers) having a length-to-diameter ratio of 5:1 or more (e.g., 6:1 or more, 8:1 or more, 10:1 or more, 12:1 or more 15:1 or more, 20:1 or more).

The methods disclosed herein can also produce particles having a largest dimension, e.g., diameter, of less than, e.g., 2000 nm, 1000, 750, 500, 250, 100, 50, 25, 20, 10, 5, or even 1 nm.

The methods disclosed herein can produce materials having a reduced bulk density. For example, the bulk density of the materials produced using the methods disclosed herein can be 0.8 g/cm$^3$ or less (e.g., 0.6, 0.5, 0.4, 0.3, 0.2 or less, e.g., 0.1 g/cm$^3$).

The methods disclosed herein can produce materials having relatively thin cross-sections, due to the combined effects of cooling the material to increase its brittleness, and processing the material using any one or more of the techniques disclosed herein. In general, materials having thin cross-sections can be cooled more efficiently than materials having thicker cross-sections; as a result, the costs (e.g., energy consumption) for material processing (e.g., particularly the costs for energy consumption in processing techniques) can be reduced.

In one aspect, the invention features a method that includes cooling a material having more than one component and an interface between the components to a temperature at which the components separate at the interface. The cooled material can then be processed to produce a product that is different, e.g., chemically different, from the material itself. For example, biomass can be cooled and then processed to produce ethanol.

Some implementations include one or more of the following features. The material can be or include biomass, e.g., in some cases the material comprises a lignocellulosic material. The components can include lignin and cellulose. The temperature can be less than or equal to the brittle point of the material. The method can further include irradiating the material, e.g., with electron beam radiation. The method can further include mechanically treating the material, e.g., by grinding, milling, or comminution. For example, mechanically treating the material can include freeze grinding or freeze milling the material. Cooling can include pre-cooling the material prior to freeze grinding or freeze milling. The components can have different coefficients of thermal expansion. The method may include temperature cycling the material. The material can be or include a hydrocarbon-containing material.

In another aspect, the invention features a method comprising processing a material to make a product, the material having been produced by treating a starting material to embrittle the starting material and processing the embrittled material to produce a product different from the embrittled material. In some implementations, the method further includes grinding or comminuting the embrittled material.

Some implementations include one or more of the following features. Treating can include cooling the starting material. Alternatively or in addition, treating can include irradiating or oxidizing the material. The starting material can include biomass or a hydrocarbon-containing material. Treating and grinding or comminuting can be performed simultaneously, e.g., in a freeze grinding or freeze milling device. Processing the material can include contacting the material with an enzyme and/or a microorganism. Treating can include temperature cycling the starting material. The biomass can include lignocellulosic material, and the method can further include separating lignin from cellulose.

In a further aspect, the invention features a method that includes cooling a biomass material to reduce the recalcitrance of the material, and, after cooling, processing the cooled material to produce a product that is different, e.g., chemically different, from the biomass material. In some implementations processing comprises contacting the material with an enzyme and/or a microorganism, e.g., saccharifying the material with an enzyme or fermenting the material with a microorganism.

Some implementations include one or more of the following features. The material can include cellulose, and contacting the material can include utilizing an enzyme to saccharify the cellulose. The method can further include irradiating the biomass material. Cooling can be performed in a freeze grinding or freeze milling device. Contacting the material can include utilizing a microorganism to produce an alcohol. Cooling can include cooling the material to a temperature below the brittle point of the material.

In other aspects, the invention features a method that includes processing, such as by mechanical processing, a biomass material or a petroleum containing material to reduce a dimension such as a particle size of the biomass material or petroleum product; and either cooling the material to a temperature of 273 K or less prior to processing, or maintaining the material at a temperature of 273 K or less during the processing.

In some implementations, the method further includes contacting the processed material with an enzyme and/or a microorganism. In some cases, the method includes sonicating the material, and/or treating the material with charged particles. Cooling may embrittle the material, which may cause separation of components of the material at an interface.

The invention also features products formed by any of the methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This application incorporates by reference herein the entire contents of each of the following applications: WO 2008/073186; and U.S. Ser. Nos. 12/417,699, 12/417,707, 12/417,720, 12/417,723, 12/417,731, 12/417,786, 12/417,840, 12/417,880, 12/417,900, 12/417,904, 12/429,045, and 12/486,436.

Other features and advantages will be apparent from the description, drawings, and claims.

DETAILED DESCRIPTION

Figure 1:
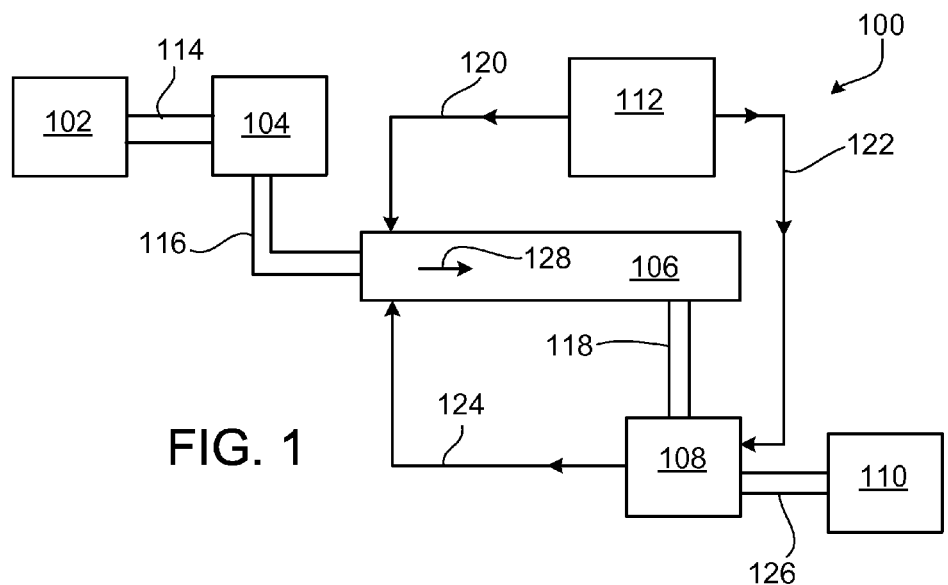
FIG. 1 is a schematic diagram showing a biomass processing system.

Certain types of materials, including cellulosic and/or lignocellulosic materials, can include significant fractions of lignin bound to cellulose and/or hemicellulose in a complex polymeric framework structure. Without wishing to be bound by theory, some evidence suggests that lignin may be bound covalently to both cellulose and hemicellulose in materials (see, e.g., Karlsson et al., Journal of Pulp and Paper Science 27: 196-201 (2001)). Further, it has generally been observed that separating lignin from cellulose and/or hemicellulose increases yields of sugars, alcohols, and other products derived from further processing of cellulose and/or hemicellulose. Further, the separating of the lignin from cellulose and hemicellulose creates a valuable co-product—the lignin itself.

Examples of biomass materials can include any biomass material that is or includes carbohydrates composed entirely of one or more saccharide units or that include one or more saccharide units can be processed by any of the methods described herein. For example, the biomass material can be cellulosic or lignocellulosic materials, starchy materials, such as kernels of corn, grains of rice or other foods, or materials that are or that include one or more low molecular weight sugars, such as sucrose or cellobiose.

For example, such biomass materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these.

Biomass also includes cellulosic fiber sources, including paper and paper products (e.g., polycoated paper and Kraft paper), and lignocellulosic fiber sources, including wood, and wood-related materials, e.g., particle board. Still other biomass includes natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic sources can be obtained from virgin scrap textile materials, e.g., remnants, or they can be post consumer waste, e.g., rags. When paper products are used, they can be virgin materials, e.g., scrap virgin materials, or they can be post-consumer waste. Aside from virgin raw materials, post-consumer, industrial (e.g., offal), and processing waste (e.g., effluent from paper processing) can also be used. Also, the fiber source can be obtained or derived from human (e.g., sewage), animal or plant wastes. Additional biomass sources have been described in U.S. Pat. Nos. 6,448,307, 6,258,876, 6,207,729, 5,973,035 and 5,952,105.

Separating lignin from cellulose and/or hemicellulose can be both time-consuming and costly. Processing techniques, including methods such as grinding and milling, can be limited in their efficiency by the strong bonds that bind the lignin to cellulose and hemicellulose.

Many processing methods—including mechanical methods, exposure to radiation, sonication, and even some chemical processing steps—generate heat in the material. While additional process heat can be advantageous in some embodiments, large quantities of heat generated by certain processing steps can also lead to thermal alteration of cellulose and/or hemicellulose, reducing yields of sugars, alcohols, and other products produced from the cellulose and/or hemicellulose.

Moreover, by example, when lignin is heated (e.g., by process heat generated during processing steps) above its glass transition temperature, the lignin can become softer and more deformable (e.g., less brittle), and therefore more difficult to process.

The methods disclosed herein use cooling techniques, e.g., cryogenic cooling techniques, for example to ensure that undesired thermal decomposition, e.g., of cellulose and/or hemicellulose, does not occur during material processing. Cooling can also be used to adjust properties of the material to improve the efficiency of separation, for example of lignin from cellulose and/or hemicellulose.

In particular, the cooling methods disclosed herein can be used alone or in combination to increase the brittleness of materials, making the cooled materials more amenable to separation via one or more processing methods such as one or more processing steps (e.g., grinding, milling, agitating, abrading, chopping, shearing), one or more radiation processing steps (e.g., exposure to charged particles such as electrons and/or ions), one or more sonication processing steps, one or more chemical processing steps (e.g., using agents such as acids, bases, oxidizing agents, reducing agents, and/or solvents), and/or one or more thermal processing steps (e.g., pyrolysis, in the presence of oxidizing and/or other agents, and/or in reduced pressure environments). By increasing the brittleness of the material by cooling and improving the efficiency with which the material by cooling can be processed, e.g., by communution or separation, processing costs (e.g., energy-related processing costs) can be reduced and intended product yields can be increased.

Moreover, when a multi-component material is cooled, different components thereof will contract and/or expand at different rates and/or in different amounts. In certain embodiments, this process can lead to breakage of chemical bonds in the material. For example, this cooling behavior can introduce stresses between bound components, leading to processes such as delamination, fracturing, peeling, disassociation, and separation of the bound components. As a result, the efficiency with which the components can be separated—and the yields of various intended products derived from the material—can be increased or decreased or kept in balance.

Cooling, alone or in combination with other treatments such as irradiation and/or oxidation, can be used to control the functionalization of the fibrous material, i.e., the functional groups that are present on or within the material. The functionalization of the material can increase solubility and/or dispersibility and can make the material more susceptible to conversion by enzymes and/or microorganisms.

In some embodiments, after the material is treated from about 1 out of every 2 to about 1 out of every 250 saccharide units includes a carboxylic acid group, or an ester or salt thereof; whereas the native or unprocessed base material can have less than 1 carboxylic acid group per 300 saccharide units. In other embodiments, from about 1 out of every 5 to about 1 out of every 250 saccharide units, e.g., 1 out of every 8 to about 1 out of every 100 units or from 1 out of 10 to about 1 out of 50 units includes a carboxylic acid group, or an ester or salt thereof.

In some embodiments, in the irradiated material from about 1 out of every 5 to about 1 out of every 1500 saccharide units includes a nitrile group, a nitroso groups or a nitro group. In other embodiments, from about 1 out of every 10 to about 1 out of every 1000 saccharide units, e.g., 1 out of every 25 to about 1 out of every 1000 units or from 1 out of 35 to about 1 out of 750 units includes a nitrile group, a nitroso groups or a nitro group.

In some embodiments, the saccharide units include mixtures of carboxylic acid groups, nitrile groups, nitroso groups and nitro groups. Mixed groups can enhance the solubility of a cellulosic or lignocellulosic material. The treated material can also include functional groups selected from the group consisting of aldehyde groups, ketone groups, amino groups, alkyl amino groups, alkyl groups, chloroalkyl groups, chlorofluoroalkyl groups, and enol groups.

FIG. 1 shows a schematic diagram of a biomass processing system 100. System 100 includes a material storage unit 102, a first material processing sub-system 104, a cooling conduit 106, a second material processing sub-system 108, a processed material reservoir 110, and a cooling fluid supply unit 112. During operation, material stored in storage unit 102 is transported via conduit 114 to first material processing sub-system 104.

Sub-system 104 can include a variety of different processing units. For example, in some embodiments, sub-system 104 can include one or more mechanical processing units (e.g., grinding units, agitation units, milling units, abrasion units, chopping units, shearing units). In certain embodiments, sub-system 104 can include one or more radiation processing units. The radiation processing units can include charged particle sources (e.g., electron beam sources and/or ion sources), in which the material is exposed to charged particles to cause alteration of the material. In some embodiments, sub-system 104 can include one or more sonication units, in which material is exposed to ultrasonic waves to alter the material. In certain embodiments, sub-system 104 can include one or more pyrolysis units and/or one or more chemical processing units. In some embodiments, sub-system 104 can include one or more steam explosion processing units. In some embodiments, sub-system 104 can include one or more combinations of these processing units.

Figure 2:
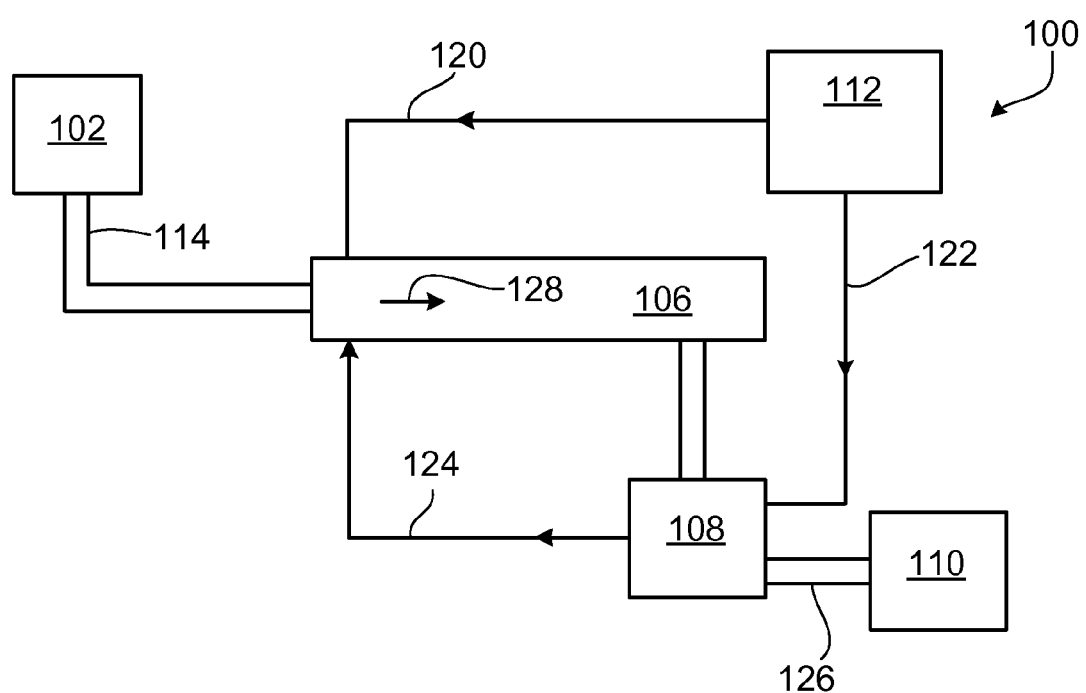
FIG. 2 is a schematic diagram showing a biomass processing system.

In general, sub-system 104 can include any one or more of the above processing units, in any combination. Sub-system 104 is generally configured to provide an initial stage of alteration of the material, in preparation for further processing steps. In some embodiments, sub-system 104 may not be present at all, and material may be transferred directly from storage unit 102 to cooling conduit 106. FIG. 2 shows an embodiment of a material processing system that does not include a processing sub-system 104. The various components in FIG. 2 have been discussed above in connection with FIG. 1, and their descriptions are not repeated at this point.

Referring again to FIG. 1, after the material has been processed in sub-system 104, e.g., by cutting, chopping, shearing, or shredding, the material is transferred via conduit 116 to cooling conduit 106. Cooling fluid supply unit 112 supplies cooling fluid (e.g., liquid nitrogen and/or cooled nitrogen gas, and/or liquid helium and/or cooled helium gas, and/or liquid argon and/or cooled argon gas, and/or solid $CO_2$ and/or liquid $CO_2$, and/or liquid air and/or cooled gaseous air) to cooling conduit 106 via conduit 120. The material is transported through cooling conduit 106 in the direction shown by arrow 128. As the material moves through conduit 106 (e.g., on a transport device such as a conveyor belt and/or an auger), the material is cooled via heat exchange with cooling fluid supplied by cooling fluid supply unit 112.

When the material reaches the end of cooling conduit 106, the material is transported through conduit 118 to second material processing sub-system 108. In some embodiments, cooling fluid supply unit 112 supplies cooling fluid via conduit 122 to second sub-system 108, as shown in FIG. 1. In general, second processing sub-system 108 can include one or more of any of the processing units disclosed herein in connection with first processing sub-system 104. Exemplary processing units include one or more processing units such as grinding, chopping, or shearing units, radiation processing units, sonication processing units, pyrolysis processing units, steam explosion processing units, and chemical processing units. Cooling fluid can be recycled for further use in cooling conduit 106 by transporting the fluid via conduit 124.

The processed material, after emerging from second processing sub-system 108, is transported to material reservoir 110 through conduit 126. Once in reservoir 110, the material can be subjected to further processing steps, including any one or more additional steps from among those disclosed in connection with processing sub-systems 104 and 108 above. Alternatively, or in addition, the processed material can be subjected to additional processing steps, including one or more processes using biological agents such as enzymes and/or microorganisms, such as bacteria and/or yeast and various chemicals and chemical formulations and solutions.

In general, the cooling methods disclosed herein can be used with a wide variety of different biomass and other material processing techniques. Exemplary techniques that can be used with the cooling methods discussed herein are disclosed, for example, in the following patent applications: WO 2008/073186; and U.S. Ser. Nos. 12/417,699, 12/417,707, 12/417,720, 12/417,723, 12/417,731, 12/417,786, 12/417,840, 12/417,880, 12/417,900, 12/417,904, 12/429,045, and 12/486,436. The disclosed cooling methods can generally be used before, during, and/or after any of the processing techniques described above are implemented.

Any of the processes disclosed herein, e.g., such as communition, can in some embodiments be particularly advantageous when used in combination with one or more cooling methods, e.g., cryogenic cooling methods. Without wishing to be bound by theory, it is believed that the increased brittleness of the lignocellulosic material that results from cooling the material assists in at least partially separating components, e.g., at an interface. Further, by increasing the brittleness of a material, it is believed that techniques may be more effective at breaking up a material—in effect, the material (and, by way of example, the lignin fraction of a material) can be transformed from a deformable, flexible polymer to a glass-like, rigid material that can be "shattered."

Figure 3:
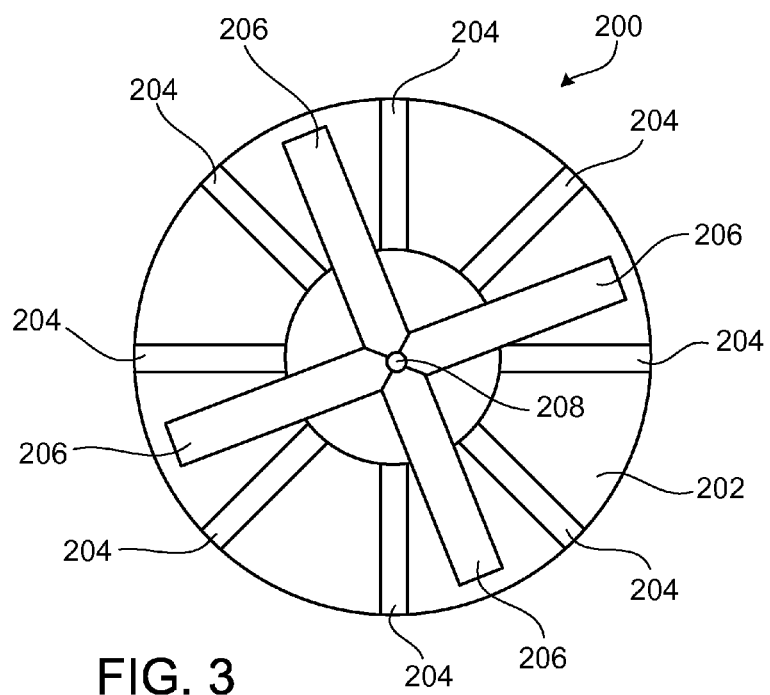
FIG. 3 is a schematic diagram showing a milling unit.

FIG. 3 shows an exemplary embodiment of a milling unit 200 that can form a portion of either or both of processing sub-systems 104 and 108. Milling unit 200 includes a conduit 202 through which material is transported. Fixed blades 204 are positioned within the conduit. Rotating blades 206 are attached to a centrally positioned shaft 208. During operation, the material is milled through the cutting action of blades 204 and 206.

Commercially available freeze milling, freeze grinding, cryomilling and cryogrinding equipment may be used. Such equipment combines cooling of the material with comminution of the material. Examples of a commercially available cryogrinding devices include the Freezer/Mill 6870, available from SPEX CertiPrep, Metuchen, N.J., and the cryogenic grinding devices available from Pulva Corporation, Saxonburg, Pa. Other suppliers include Air Products, Praxair, and Air Liquide. In some embodiments, the equipment may include a pre-cooling area, e.g., a cooling conveyor such as a cooled screw extruder. In some cases liquid nitrogen is sprayed onto the material to be cooled in the pre-cooling area. The grinding may be provided, for example, by a reciprocating pin or other element. For example, the grinding device may be a pin mill. It is generally preferred that the temperature of the material be monitored and controlled throughout feeding and grinding.

Freeze grinding may be combined with irradiation, in which case irradiation can be performed before, during, or after freeze grinding. In some cases, freeze grinding can reduce the amount of radiation that is needed to reduce the recalcitrance of a biomass material or process a hydrocarbon-containing material.

Sonication processing techniques can, in certain embodiments, be particularly advantageous when used in combination with, e.g., before, immediately after, or during, the cooling methods disclosed herein. In general, sonication processing of material is effective at altering the material due to heat supplied to the material via mechanical waves (e.g., sound waves). When cooling methods are used to reduce the temperature of the material, the material becomes more brittle, and is less able to deform in response to incident mechanical waves and/or undergo rapid expansion due to local heating. As a result, the efficiency with which sonication effectively changes the material is increased.

In some embodiments, techniques that use radiation (e.g., electron beams and/or ion beams) to process material can be particularly advantageous when used in combination with, e.g., before, immediately after, or during, cooling of the material. For example, in certain embodiments, material can first be irradiated (e.g., in sub-system 104) before it is cooled. Alternatively, the material can first be cooled, and then irradiated (e.g., in sub-system 108). The radiation dose may be, for example, from about 0.1 MRad to 200 Mrad, e.g., from about 10 MRad to 100 Mrad or about 30 MRad to 90 MRad. The radiation may be delivered in a single irradiation step or multiple irradiation steps, and the material can be cooled between irradiation steps if desired. Such cooling is described in U.S. Ser. No. 12/417,880.

Exposure of the material to certain types and dosages of radiation may increase the brittleness of the material. The material can be cooled to decrease its temperature and further increase its brittleness. During and/or after the cooling of the material, the material can be processed (e.g., via milling, grinding, shearing, and other such techniques) to alter the material in preparation for further processing steps that produce useful products. Alternatively, or in addition, radiation exposure (e.g., electron beam exposure and/or ion beam exposure) of the material after cooling the material can also be used to further alter the material and/or make the material more brittle. When both radiation exposure and cooling are used to make the material more brittle, product yields (e.g., ethanol and/or other alcohols) can be significantly increased, and the amount of energy required to process the material can be reduced.

In certain embodiments, multiple cooling and mechanical processing stages, or alternating cooling and heating stages, e.g., with our without additional mechanical or other physical processing, can be used to process a material, e.g., biomass. For example, each successive stage can further reduce the average size of the biomass particles, until a desired particle size is reached. Each cooling stage can be similar or different (e.g., the system can include a plurality of similar cooling sub-systems). In some embodiments, the system can include a single cooling sub-system through which the material passes multiple times. Alternatively, in certain embodiments, different cooling stages (e.g., cooling stages that cool the biomass to different temperatures, such as progressively lower temperatures) can be used to process the material.

Similarly, in certain embodiments, multiple mechanical processing stages can be used to process biomass or other materials such as petroleum products. The materials can be recirculated through the same processing unit multiple times, and/or the system can include multiple mechanical units. The units can all be similar to one another, or some of the units can differ (e.g., in structure) from one another.

In general, a wide variety of different cooling fluids can be used to cool the material. In the embodiments discussed above, liquid and/or cold gaseous nitrogen was used as the cooling fluid. However, in some embodiments, one or more other cooling fluids can be used, including liquid helium, liquid oxygen, liquid hydrogen, liquid air, other such fluids, and combinations thereof. In certain embodiments, the fluids can be gases rather than liquids, or can include solids (e.g., ice, solid $CO_2$) mixed with, or instead of, the liquids. For example, a wide variety of cooled gases (including cooled noble gases, cooled nitrogen gas, cooled oxygen gas, and cooled hydrogen gas) can be used in place of, or together with, liquid cooling fluids.

In certain embodiments, solids can be added to the materials to assist in processing the materials. For example, solid $CO_2$ can be added to the materials to assist in altering the materials in one or more processing units. Other solids that could also be used include ice, for example. The solid may also be a solid element that is later removed or separated from the material, e.g., one or more balls, pins, or other solid milling elements.

The temperature to which the material is cooled depends upon a number of factors, including the processing techniques that are used to alter the material and the nature of the material. In some embodiments, for example, the material is cooled to a temperature less than the glass transition temperature of lignin, which is about 100° to 170° C., e.g., about 120° to 150° C., e.g., about 125° C. When the lignin is cooled below its glass transition temperature, it changes from a soft, deformable material to a brittle, glassy material. The brittle, glassy lignin can be more readily altered by various processes, including the processes disclosed above. Further, by cooling the lignin below its glass transition temperature the physical structure of the lignin can be changed. Changes to the lignin structure can lead to internal stresses within the material where the lignin is bound to cellulose and/or hemicellulose. These internal stresses can lead to delamination and thus separation of the lignin from the cellulose and/or hemicellulose. In some implementations, the material is cooled below the temperature at which the material becomes brittle (the "brittle point" of the material). This brittle point of a particular material can be measured using commercially available testing equipment, e.g., the Benz BPT2100 Brittlepoint Tester available from Benz Material Testing Instruments, Providence, R.I.

In some embodiments, the material can be cooled below a glass transition temperature of one or more other elements or components in the material, such as hemicellulose. Similar considerations to those that are discussed above in connection with lignin apply to hemicellulose as well. In particular, cooling of the hemicellulose can make it more brittle, improving the efficiency of subsequent processing steps. Cooling can also introduce internal stresses within the biomass structure, which can lead to separation of the hemicellulose from other components (e.g., cellulose) in the material.

In certain embodiments, the material can be cooled to a temperature of 400 K or less (e.g., 380 K or less, 360 K or less, 340 K or less, 320 K or less, 300 K or less, 280 K or less, 260 K or less, 240 K or less, 220 K or less, 200 K or less, 150 K or less, 100 K or less, 80 K or less, 77 K or less, 70 K or less, 50 K or less). In some embodiments, the material can be cooled to a temperature less than or equal to room temperature (e.g., 293 K). In certain embodiments, the material can be cooled to about the temperature of liquid nitrogen (e.g., 77 K) or less. Cooling the material to temperatures less than the temperature of liquid nitrogen can be achieved by using cooling fluids with a lower boiling point than liquid nitrogen (e.g., liquid helium).

In some embodiments, the rate at which the material is cooled can be controlled to assist in separating components of the material. For example, by cooling the material rapidly, lowest-energy arrangements of the associated components in the biomass may not have time to form. In other words, the cooled material may be in an energy state that is not a minimum energy state, and can therefore be unstable and more readily altered using further processing steps. In certain embodiments, for example, the rate at which the material is cooled is 1 K/s or more (e.g., 2 K/s or more, 3 K/s or more, 5 K/s or more, 7.5 K/s or more, 10 K/s or more, 15 K/s or more, 20 K/s or more, 30 K/s or more, 40 K/s or more, 50 K/s or more, 75 K/s or more, 100 K/s or more, or even more).

In certain embodiments, using the processing systems disclosed herein, the material can be maintained at a selected temperature and/or within a selected temperature range during processing of the material using any one or more of the various processing techniques disclosed herein. For example, the material can be maintained at a temperature of 400 K or less (e.g., 380 K or less, 360 K or less, 340 K or less, 320 K or less, 300 K or less, 280 K or less, 260 K or less, 240 K or less, 220 K or less, 200 K or less, 150 K or less, 100 K or less, 80 K or less, 77 K or less, 70 K or less, 50 K or less). In some embodiments, the material can be maintained at or below room temperature (e.g., 293 K). In certain embodiments, the biomass can be maintained at the temperature of liquid nitrogen (e.g., 77 K) or less.

In certain embodiments, the material can be subjected to a sequence of heating and cooling stages that are selected to cause further disruption to the association (e.g., suspected covalent bonds) between lignin and cellulose and/or hemicellulose. Rapid thermal cycling of the material can introduce internal stresses within the material, which can lead to separation of biomass components (e.g., without further processing, or as a result of further processing steps).

In addition, a variety of different agents can be added to the material prior to, during, and/or following cooling of the material. Exemplary agents that can be added include water (and, more generally, any other compounds that expand or contract when cooled), oxidizing agents, reducing agents, acids, bases, and materials that contract significantly upon cooling. In general, agents such as water can be introduced into one or more of the components of the material to cause swelling of the components when hydrated. For example, when the material, e.g., biomass, is cooled, the water expands and/or contracts, creating periodic internal stresses in the material that can lead to cleavage of bonds within the material, e.g., between lignin and cellulose and/or hemicellulose. Other agents that undergo sublimation (e.g., carbon dioxide) can also be used to produce similar results. Agents that sublime generally undergo significant changes in molar volume at a phase transition. Such agents can be introduced into the material to further promote separation of the components therein when relatively rapid expansion and/or contraction of the material occurs as a result of the added agents.

As noted above, various chemical agents such as oxidizing agents and/or reducing agents and/or acids and/or bases can be added to the material. The various agents can react with the material before, during, and/or after cooling to further assist in altering the material prior to product formation and extraction. In general, certain components of the material may be stable in the presence of one agent, but reactive in the presence of other agents. For example, cellulose is stable to bases, but is altered by acids. By introducing bases into one or more of the various processing sub-systems, one or more selected component(s) of the material, e.g., lignin, can be selectively altered and disassociated from other component(s), e.g., cellulose and/or hemicellulose, improving yields of products derived from the material. Chemical agents can be added to the various processing sub-systems as liquids, in solutions, and/or as gases. In some embodiments, the agents can be introduced in gaseous form, and can be condensed into liquids as the material is cooled.

In certain embodiments, various chemical oxidizing and/or reducing agents can be added before, during, and/or after cooling to promote separation of at least some of the material components via chemical reactions. Cooling alone, or together with one or more of the processing techniques disclosed above, can be used to promote disassociation, e.g., of lignin from cellulose and/or hemicellulose. This disassociation can be further promoted by reacting cellulose, hemicellulose, and/or lignin with agents such that the products of such reactions do not re-associate as readily. Exemplary oxidizing and reducing agents include ozone, oxygen, air, ammonia, and a wide variety of other agents.

In some embodiments, multiple different cooling stages can be used, each of which is configured to cool the material to a different temperature. For example, in an initial stage of processing, the material can be cooled to a selected temperature and can be processed (e.g., mechanically, with radiation exposure, with sonication, and/or with various other techniques). For example, in each subsequent stage of processing, as the material particles can be made increasingly smaller, the material can be cooled to successively lower temperatures and further processed, to continue to reduce the size of the particles and/or further disassociate components of the material such as biomass (e.g., disassociate lignin from cellulose and/or hemicellulose) or to change the structure.

In general, the disclosure is not limited to the specific processing system disclosed above in FIG. 1. In particular, a number of different cooling methods can be used to reduce the temperature of the material before, during, and/or after the application of various processing techniques. Further, in general, a wide variety of different cooling sub-systems can be used to cool the material.

In some embodiments, the processing systems disclosed herein can include a separation sub-system that functions to separate various components of the material after the material has been cooled and processed. For example, when material is processed to disassociate lignin from cellulose and/or hemicellulose, the processing system can include a separation sub-system configured to remove the disassociated lignin. Various methods, including physical separation methods such as decanting, centrifuging, distillation, and extraction can be used to separate the components, e.g., the lignin from the other components of a lignocellulosic material, or sand from hydrocarbons in an oil sand. Other methods which can be implemented in the separation sub-system include thermochemical processing, chemical processing, and radiation exposure processing).

In certain embodiments, the processing systems disclosed herein can include one or more wetting stations to introduce various wetting agents—particularly water and/or other liquids such as dimethyl sulfoxide—into the materials. For example, following mechanical processing units such as the milling unit shown in FIG. 3, the processing system can include a sprayer that adds water and/or other agents to the material. The sprayer can create a fine mist that settles on surfaces of the material's particles. If the material is cooled during or after the mist is applied, the mist can be frozen onto the surfaces of the particles to ensure adhesion. The temperature of the material can undergo one or more heating-cooling cycles to further swell the material with the applied mist. Further, in certain embodiments, changes, e.g., rapid changes, in the temperature of the material can further alter the material structure.

In some embodiments, multiple wetting stages can be used. Each of the multiple wetting stages can introduce the same agent into the material, or different stages can introduce different agents. The selection of which agents to introduce depends upon factors such as the intended application of the material, the physical-chemical state of the material, and the conditions in subsequent material processing stages.

Systems and methods for enhancing wetting of materials before, during, and after processing are disclosed, for example, in U.S. Ser. No. 12/417,880, the disclosure of which is incorporated herein by reference.

In some embodiments, after the materials have been processed using the methods disclosed herein, the processed materials can be subjected to additional processing steps. In particular, the processed materials can be contacted with biological agents such as enzymes, and/or with microorganisms such as yeast (e.g., P. Stipitis) and/or bacteria to extract a variety of useful products from the processed materials, including products such as hydrogen, alcohols (e.g., ethanol and/or butanol), organic acids (e.g., acetic acid), hydrocarbons, co-products (e.g., proteins) or mixtures of any of these. Suitable biological agents and microorganisms for further processing of materials are disclosed, for example, in WO 2008/073186.

For example, in some embodiments the techniques described herein are used to separate and remove lignin from a lignocellulosic material, and then the remaining cellulosic components are saccharified, e.g., using an enzyme. The removal of the lignin reduces the recalcitrance of the material, allowing the conversion of the cellulose to sugars, which can then be fermented to produce alcohols.

EXAMPLE

Various samples of cellulosic materials were tested in shake flasks, using P. stipitis NRRL Y-7124 and a standard nutrient medium recipe at various levels. The ethanol concentration was measured over time for each of the flasks. As noted below (see Legend for Table 1), the cellulosic samples were derived from cut grass (CG). Some of the samples were freeze ground (FG), using a SPEX Certiprep® Freezer/Mill 6870. The freeze grinding conditions were as follows: 4 minutes pre-cool, followed by three cycles of 10 minutes run time and 2 minutes cooling time, with a grinder frequency of 15 Hz. Some of the samples were irradiated without freeze grinding, while others were irradiated after freeze grinding. Irradiation was performed using an electron beam. The radiation dose is indicated by the number after the "CG," with 0.2E indicating 0.2 MRads, 0.4E indicating 0.4 MRads, etc. Where the radiation dose was 10 MRad or less, it was delivered in a single pass. Where the radiation dose was greater than 10 MRad, it was delivered in multiple 10 MRad passes (e.g., 50 MRad=5×10 MRad), with 1 minute intervals between passes to allow the material to cool at ambient temperature.

Reagents Used

| Media Component | Manufacturer | Reference # | Lot # |
|---|---|---|---|
| Urea | ScholAR Chemistry | 9472706 | AD-7284-43 |
| Yeast Nitrogen Base | Becton Dickinson | 291940 | 7128171 |
| Peptone | Becton Dickinson | 211677 | 4303198 |
| Xylose (>98%) | Alfa Aesar | A10643 | 10131481 |
| Glucose (>98.9%) | Fisher | BP-350-1, 50-99-7 | 030064, 030439 |
| YM Broth | Becton Dickinson | 271120 | 6278265 |
| Novozyme® 188* | Novozymes | Sigma C6105 | 018K0735, 058K1144 |
| Celluclast 1, 5 FG | Novozymes | Sigma C2730 | 077K0735, 058K1144 |

-continued

Reagents Used

| Media Component | Manufacturer | Reference # | Lot # |
|---|---|---|---|
| Optimash™ TBG enzyme** | Genencor® | N/A | 1600925859 |

*Cellobiase from Aspergillus niger
**β-glucanase EC 3.2.1.6.

Cell Bank Preparation and Seed Flask Development

To preserve the original culture, a working cell bank of each culture was prepared. A working cell bank of P. stipitis NRRL Y-7124 was prepared from a rehydrated lyophilized culture obtained from ARS Culture Collection. Cryovials containing P. stipitis culture in 15% v/v glycerol were stored at −75° C.

To prepare the seed flask, a portion of the thawed working cell bank material was streaked onto a Yeast Mold (YM) Broth+20 g/L agar (pH 5.0) and incubated at 30° C. for 2 days. The plates were held for 2 days at 4° C. before use. One colony from the Yeast Mold Agar was used to inoculate a 250 mL Erlenmeyer flask containing 100 mL of sterile broth (40 g/L glucose, 1.7 g/L yeast nitrogen base, 2.27 g/L urea, 6.56 g/L peptone, 40 g/L xylose, pH 5.0) and incubated for 24 hours at 25° C. and 150 rpm. After 23 hours of growth, a sample was taken and analyzed for optical density (OD 600 nm in a UV spectrophotometer), total cell count, and purity (Gram stain). Based on these results, a flask with an OD of between 6 and 11 and a cell count of 2 to 6×10$^8$ cells/mL was used to inoculate the test flasks. One mL of seed flask contents was added to the 100 mL test flasks (1% v/v).

Test Flasks

The test flasks were 250 mL Erlenmeyer flasks containing 100 mL of broth. The test flasks contained the Standard Medium (1.7 g/L yeast nitrogen base, 2.27 g/L urea, 6.56 g/L peptone, pH 5.0.) There were three sets of control flasks because the testing was done over a three week span and control flasks were analyzed for each week of testing.

The timeline of activities was as follows. The lignocellulosic sample (7.77 g) was combined with 100 mL of sterile broth in a sterile 250 mL flask and allowed to soak for 14 hours at room temperature. After the soak, the pH of the flask contents was adjusted to 5.0 with 1 N NaOH. Once the pH was adjusted, 3.89 mL of Celluclast 1,5 FG, 0.77 mL Novozyme® 188, and 0.77 mL Optimash™ TBG was added and the flasks were incubated at 50° C. for 21 hours.

After the enzyme treatment, the pH of the flask contents was adjusted to 5.5, 6.0, or 6.25. After pH adjustment, flasks were inoculated with 1 mL of P. stipitis seed flask contents and incubated for 96 hours at 25° C. and 125 rpm.

Three control flasks (two positive, one negative) were inoculated each week, nine in total. Two positive control flasks contained sugars. One contained 80 g/L sugars (40 g/L glucose and 40 g/L xylose), the other contained 30 g of sugars (15 g/L glucose and 15 g/L xylose). There were no sugars added to the negative control flask.

One set of flasks (five in total) contained xylose-only broth (40 g/L xylose 1.7 g/L yeast nitrogen base, 2.27 g/L urea, 6.56 g/L peptone) at pH 4.5, 5.0, 5.5, 6.0, 6.5. The flasks were incubated at 125 rpm and 25° C. after inoculation with 1 mL of P. stipitis.

A second set of flasks (five in total) contained the xylose-only broth (40 g/L xylose 1.7 g/L yeast nitrogen base, 2.27 g/L urea, 6.56 g/L peptone) at pH 4.5, 5.0, 5.5, 6.0, 6.5. The flasks were incubated at 250 rpm and 25° C. after inoculation with 1 mL of P. stipitis.

During week 1, samples CG0.4E and CG0.4E-FG4102315 were tested in flasks at pH 5.5. However, the protocol indicated that they should be tested at both 5.5 and 6.0. Therefore, both samples were tested at pH 5.5 and 6.0 in week 2 of the experiment (flasks 28 through 31).

Analysis

A total of eight samples were taken from each flask at 0, 12, 24, 36, 48, 60, 72, and 96 hours post-inoculation and analyzed for glucose, ethanol, and xylose concentration using the YSI Biochem Analyzer (YSI, Interscience). Samples were centrifuged at 14,000 rpm for 20 minutes and the supernatant stored at −20° C. A standard was analyzed daily to ensure the integrity of the membrane was maintained.

The cell count of each seed flask was analyzed in order to determine the initial cell concentration in the test flasks. One sample at 72 hours of incubation was taken from each flask analyzed for cell count. Appropriately diluted samples were mixed with 0.05% Trypan blue and loaded into a Neubauer haemocytometer. The cells were counted under 40× magnification.

The pH of each flask was measured at 0, 12, 24, 36, 48, 60, 72, and 96 hours.

Results

The number of cells in the seed flasks was analyzed. During week 1 (Flasks 1 through 27), the seed flask cell concentration was $5.03 \times 10^8$ cells/mL. Therefore, the starting cell concentration in the test flasks was $5.03 \times 10^6$ cells/mL. During week 2 (Flasks 28 through 64), the number of cells in the seed flask was $6.38 \times 10^8$ cells/mL. Therefore, the starting concentration of cells in the test flasks was $6.38 \times 10^6$ cells/mL. During week 3 (Flasks 65 through 105), the number of cells in the seed flask was $5.93 \times 10^8$ cells/mL. Therefore, the starting concentration of cells in the test flasks was $5.93 \times 10^6$ cells/mL.

The ethanol concentration in each of the flasks during incubation is listed in Table 1 below:

TABLE 1

| Flask No. | Sample No. | Start pH | Ethanol Concentration (g/L) at Incubation Time (h) | | | | | | | |
|---|---|---|---|---|---|---|---|---|---|---|
| | | | 0 | 12 | 24 | 36 | 48 | 60 | 72 | 96 |
| 1 | CG | 5.5 | 0.10 | 0.14 | 0.16 | 0.05 | 0.03 | 0.04 | 0.05 | 0.07 |
| 2 | CG | 6.0 | 0.12 | 0.21 | 0.24 | 0.19 | 0.14 | 0.09 | 0.08 | 0.07 |
| 3 | CG-FG | 5.5 | 0.10 | 1.35 | 4.34 | 4.31 | 5.75 | 5.98 | 5.54 | 3.32 |
| 4 | CG-FG | 6.0 | 0.10 | 1.44 | 4.33 | 4.12 | 6.59 | 6.46 | 5.71 | 3.61 |
| 5 | CG0.2E | 5.5 | 0.10 | 0.21 | 0.21 | 0.07 | 0.04 | 0.17 | 1.25 | 0.08 |
| 6 | CG0.2E-FG | 5.5 | 0.10 | 1.24 | 4.42 | 3.85 | 5.82 | 6.05 | 5.52 | 3.03 |
| 7 | CG0.4E | 5.5 | 0.10 | 0.88 | 2.13 | 2.80 | 3.95 | 3.47 | 2.54 | 0.33 |
| 8 | CG0.4E-FG | 5.5 | 0.09 | 1.33 | 4.38 | 4.38 | 5.47 | 5.76 | 5.92 | 3.83 |
| 9 | CG0.6E | 5.5 | 0.11 | 1.06 | 1.98 | 2.67 | 2.94 | 0.91 | 1.13 | 0.11 |
| 10 | CG0.6E-FG | 5.5 | 0.10 | 1.33 | 4.53 | 4.65 | 5.94 | 6.22 | 6.33 | 4.09 |
| 11 | CG0.8E | 5.5 | 0.10 | 0.60 | 2.28 | 2.75 | 4.55 | 3.99 | 2.07 | 0.12 |
| 12 | CG0.8E-FG | 5.5 | 0.10 | 0.83 | 4.36 | 4.44 | 5.62 | 5.91 | 5.43 | 3.35 |
| 13 | CG2E | 5.5 | 0.10 | 0.61 | 2.23 | 2.72 | 3.79 | 2.33 | 0.06 | 0.08 |
| 14 | CG2E-FG | 5.5 | 0.1 | 1.13 | 4.39 | 4.51 | 5.74 | 6.20 | 6.12 | 3.91 |
| 15 | CG4E | 5.5 | 0.10 | 0.66 | 2.37 | 2.78 | 3.96 | 3.56 | 2.04 | 0.12 |
| 16 | CG4E-FG | 5.5 | 0.09 | 1.16 | 4.75 | 4.45 | 5.61 | 5.94 | 6.33 | 4.04 |
| 17 | CG6E | 5.5 | 0.10 | 0.62 | 2.45 | 2.74 | 4.26 | 4.36 | 3.04 | 0.20 |
| 18 | CG6E-FG | 5.5 | 0.00 | 1.17 | 4.66 | 4.38 | 5.77 | 6.06 | 6.27 | 4.26 |
| 19 | CG8E | 5.5 | 0.10 | 0.77 | 2.18 | 2.26 | 2.36 | 2.33 | 2.10 | 1.32 |
| 20 | CG8E-FG | 5.5 | 0.11 | 1.05 | 4.78 | 4.79 | 5.70 | 6.25 | 6.23 | 3.81 |
| 21 | CG10E | 5.5 | 0.12 | 0.70 | 2.28 | 2.62 | 3.88 | 4.04 | 2.82 | 0.14 |
| 22 | CG10E | 6.0 | 0.11 | 0.64 | 2.21 | 2.20 | 3.24 | 3.84 | 3.13 | 1.02 |
| 23 | CG10E-FG | 5.5 | 0.11 | 0.99 | 4.81 | 4.92 | 5.71 | 6.25 | 6.03 | 3.98 |
| 24 | CG10E-FG | 6.0 | 0.10 | 1.28 | 4.85 | 5.12 | 6.58 | 6.88 | 6.46 | 3.90 |
| 25 | Control (80 g sugar) | 5.0 | 0.04 | 0.89 | 6.95 | 9.57 | 11.10 | 11.90 | 12.40 | 11.90 |
| 26 | Control (30 g sugar) | 5.0 | 0.06 | 1.54 | 6.09 | 6.54 | 7.63 | 8.11 | 8.17 | 6.91 |
| 27 | Control (No sugar) | 5.0 | 0.06 | 0.01 | 0.00 | 0.00 | 0.00 | 0.16 | 0.00 | 0.04 |
| 28 | CG0.4E | 5.5 | 0.09 | 0.12 | 0.15 | 0.11 | 0.15 | 0.07 | 0.84 | 0.05 |
| 29 | CG0.4E | 6.0 | 0.08 | 0.30 | 1.51 | 1.55 | 1.92 | 3.06 | 2.59 | 1.18 |
| 30 | CG0.4E-FG | 5.5 | 0.15 | 0.49 | 4.14 | 4.78 | 5.27 | 5.87 | 5.44 | 3.73 |
| 31 | CG0.4E-FG | 6.0 | 0.14 | 0.58 | 4.38 | 5.13 | 6.09 | 5.69 | 5.22 | 3.53 |
| 32 | CG20E | 5.5 | 0.18 | 0.27 | 2.55 | 2.70 | 2.71 | 3.19 | 4.14 | 2.56 |
| 33 | CG20E-FG | 5.5 | 0.14 | 0.40 | 4.98 | 5.89 | 5.46 | 5.36 | 5.58 | 3.84 |
| 34 | CG30E | 5.5 | 0.12 | 0.19 | 2.75 | 3.27 | 3.19 | 2.67 | 3.07 | 2.18 |

TABLE 1-continued

| Flask No. | Sample No. | Start pH | \multicolumn{8}{c}{Ethanol Concentration (g/L) at Incubation Time (h)} |
|---|---|---|---|---|---|---|---|---|---|---|
| | | | 0 | 12 | 24 | 36 | 48 | 60 | 72 | 96 |
| 35 | CG30E-FG | 5.5 | 0.15 | 0.30 | 5.24 | 6.33 | 6.08 | 5.83 | 6.12 | 4.91 |
| 36 | CG40E | 5.5 | 0.14 | 0.18 | 3.18 | 4.26 | 4.00 | 3.20 | 3.55 | 2.90 |
| 37 | CG40E-FG | 5.5 | 0.14 | 0.30 | 5.62 | 6.50 | 6.99 | 6.74 | 6.91 | 5.37 |
| 38 | CG50E | 5.5 | 0.17 | 0.22 | 3.06 | 4.33 | 4.27 | 3.97 | 3.60 | 3.38 |
| 39 | CG50E | 6.0 | 0.17 | 0.37 | 4.47 | 4.62 | 5.11 | 4.93 | 5.13 | 3.60 |
| 40 | CG50E-FG | 5.5 | 0.17 | 0.27 | 5.77 | 7.93 | 7.58 | 6.95 | 6.92 | 5.90 |
| 41 | CG50E-FG | 6.0 | 0.16 | 0.34 | 6.23 | 7.70 | 7.13 | 5.94 | 5.81 | 4.25 |
| 42 | CG60E | 5.5 | 0.14 | 0.18 | 4.24 | 5.76 | 5.99 | 5.58 | 5.56 | 4.33 |
| 43 | CG60E-FG | 5.5 | 0.13 | 0.25 | 6.01 | 8.36 | 8.92 | 8.42 | 8.47 | 7.63 |
| 44 | CG70E | 5.5 | 0.15 | 0.17 | 6.61 | 6.40 | 6.63 | 6.41 | 6.35 | 5.57 |
| 45 | CG70E-FG | 5.5 | 0.13 | 0.20 | 4.52 | 8.98 | 9.25 | 8.75 | 8.68 | 7.44 |
| 46 | CG80E | 5.5 | 0.13 | 0.18 | 5.13 | 7.20 | 6.93 | 6.69 | 7.12 | 5.88 |
| 47 | CG80E-FG | 5.5 | 0.14 | 0.20 | 6.96 | 9.58 | 10.20 | 9.54 | 9.03 | 8.52 |
| 48 | CG90E | 5.5 | 0.14 | 0.16 | 5.10 | 7.34 | 7.69 | 7.07 | 7.40 | 6.83 |
| 49 | CG90E-FG | 5.5 | 0.15 | 0.21 | 7.03 | 9.42 | 11.50 | 11.00 | 9.79 | 8.90 |
| 50 | CG100E | 5.5 | 0.18 | 0.20 | 5.84 | 8.05 | 8.99 | 8.52 | 8.32 | 7.14 |
| 51 | CG100E | 6.0 | 0.15 | 0.24 | 6.46 | 9.03 | 8.73 | 8.75 | 8.38 | 5.94 |
| 52 | CG100E | 6.25 | 0.16 | 0.18 | 6.45 | 9.13 | 8.88 | 8.21 | 7.78 | 6.56 |
| 53 | CG100E-FG | 5.5 | 0.13 | 0.14 | 7.30 | 8.87 | 10.90 | 10.20 | 10.40 | 9.28 |
| 54 | CG100E-FG | 6.0 | 0.13 | 0.24 | 7.30 | 10.40 | 10.50 | 10.10 | 9.73 | 8.43 |
| 55 | CG100E-FG | 6.25 | 0.13 | 0.19 | 7.33 | 10.50 | 10.70 | 10.60 | 10.00 | 8.94 |
| 56 | CG110E | 5.5 | 0.16 | 0.12 | 6.19 | 7.95 | 9.65 | 8.60 | 8.66 | 7.94 |
| 57 | CG110E | 6.0 | 0.19 | 0.22 | 6.35 | 8.76 | 9.26 | 8.70 | 8.21 | 7.12 |
| 58 | CG110E-FG | 5.5 | 0.15 | 0.14 | 7.06 | 8.80 | 10.40 | 10.10 | 9.74 | 8.88 |
| 59 | CG110E-FG | 6.0 | 0.14 | 0.19 | 7.70 | 10.50 | 11.60 | 10.90 | 10.00 | 8.57 |
| 60 | CG120E | 5.5 | 0.19 | 0.14 | 6.45 | 7.83 | 9.88 | 9.79 | 8.91 | 8.11 |
| 61 | CG120E-FG | 5.5 | 0.15 | 0.13 | 7.35 | 9.02 | 10.60 | 10.70 | 10.00 | 8.88 |
| 62 | Control (80 g sugar) | 5.0 | 0.10 | 0.54 | 5.22 | 8.46 | 9.85 | 10.90 | 11.90 | 12.50 |
| 63 | Control (30 g sugar) | 5.0 | 0.09 | 0.97 | 5.79 | 7.07 | 8.41 | 8.63 | 8.82 | 4.50 |
| 64 | Control (No sugar) | 5.0 | 0.07 | 0.04 | 0.00 | 0.00 | 0.00 | 0.00 | 0.00 | 0.00 |
| 65 | CG130E | 5.5 | 0.10 | 0.19 | 6.71 | 8.15 | 9.88 | 9.13 | 9.16 | 9.15 |
| 66 | CG130E | 6.0 | 0.11 | 0.28 | 6.62 | 9.15 | 9.86 | 9.27 | 9.20 | 8.52 |
| 67 | CG130E-FG | 5.5 | 0.11 | 0.20 | 7.42 | 8.72 | 10.50 | 10.50 | 10.10 | 9.45 |
| 68 | CG130E-FG | 6.0 | 0.11 | 0.25 | 7.08 | 9.72 | 10.30 | 10.50 | 9.87 | 8.95 |
| 69 | CG140E | 5.5 | 0.11 | 0.16 | 6.27 | 7.43 | 9.27 | 9.23 | 9.03 | 8.82 |
| 70 | CG140E | 6.0 | 0.09 | 0.22 | 6.34 | 7.90 | 9.44 | 8.94 | 8.88 | 8.17 |
| 71 | CG140E-FG | 5.5 | 0.10 | 0.17 | 7.08 | 8.22 | 9.88 | 10.10 | 9.88 | 8.80 |
| 72 | CG140E-FG | 6.0 | 0.10 | 0.30 | 7.21 | 9.50 | 10.30 | 10.20 | 9.64 | 8.72 |
| 73 | CG150E | 5.5 | 0.10 | 0.16 | 6.04 | 7.65 | 9.00 | 8.96 | 9.20 | 9.14 |
| 74 | CG150E | 6.0 | 0.9 | 0.21 | 6.89 | 8.80 | 9.92 | 9.90 | 9.69 | 8.62 |
| 75 | CG150E | 6.25 | 0.12 | 0.23 | 6.29 | 8.91 | 9.66 | 7.52 | 9.29 | 8.38 |
| 76 | CG150E-FG | 5.5 | 0.10 | 0.18 | 5.86 | 8.36 | 9.73 | 9.41 | 9.31 | 8.87 |
| 77 | CG150E-FG | 6.0 | 0.10 | 0.27 | 7.05 | 9.63 | 9.81 | 9.76 | 9.26 | 8.31 |
| 78 | CG150E-FG | 6.25 | 0.06 | 0.28 | 6.89 | 8.86 | 8.90 | 9.95 | 7.52 | 5.97 |
| 79 | CG160E | 5.5 | 0.10 | 0.12 | 6.02 | 7.55 | 8.99 | 8.70 | 8.62 | 7.92 |
| 80 | CG160E-FG | 6.0 | 0.10 | 0.20 | 6.92 | 9.11 | 9.84 | 10.10 | 9.53 | 8.58 |
| 81 | CG170E | 5.5 | 0.10 | 0.14 | 4.89 | 7.39 | 8.60 | 9.49 | 8.68 | 7.59 |

TABLE 1-continued

| Flask No. | Sample No. | Start pH | \multicolumn{8}{c}{Ethanol Concentration (g/L) at Incubation Time (h)} |
|---|---|---|---|---|---|---|---|---|---|---|
| | | | 0 | 12 | 24 | 36 | 48 | 60 | 72 | 96 |
| 82 | CG170E-FG | 6.0 | 0.11 | 0.19 | 7.18 | 8.66 | 10.10 | 9.49 | 9.16 | 7.99 |
| 83 | CG180E | 5.5 | 0.11 | 0.15 | 6.27 | 7.37 | 8.65 | 9.58 | 8.38 | 7.95 |
| 84 | CG180E-FG | 6.0 | 0.11 | 0.22 | 7.00 | 8.69 | 9.22 | 8.98 | 8.84 | 7.85 |
| 85 | CG190E | 5.5 | 0.01 | 0.15 | 5.12 | 6.92 | 8.00 | 9.50 | 8.65 | 8.37 |
| 86 | CG190E-FG | 6.0 | 0.09 | 0.17 | 6.66 | 7.92 | 9.12 | 8.87 | 8.75 | 8.03 |
| 87 | CG200E | 5.5 | 0.10 | 0.15 | 5.75 | 7.12 | 8.68 | 9.05 | 7.99 | 7.55 |
| 88 | CG200E | 6.0 | 0.08 | 0.16 | 6.38 | 8.80 | 8.92 | 8.57 | 8.30 | 6.98 |
| 89 | CG200E | 6.25 | 0.10 | 0.22 | 6.28 | 8.17 | 8.55 | 8.67 | 8.30 | 7.84 |
| 90 | CG200E-FG | 5.5 | 0.01 | 0.16 | 5.54 | 7.47 | 8.69 | 8.50 | 8.32 | 7.67 |
| 91 | CG200E-FG | 6.0 | 0.11 | 0.21 | 5.69 | 7.78 | 8.90 | 8.75 | 8.44 | 7.40 |
| 92 | CG200E-FG | 6.25 | 0.11 | 0.19 | 6.29 | 8.30 | 9.37 | 9.08 | 7.93 | 7.31 |
| 93 | Control (80 g sugar) | 5.0 | 0.02 | 0.50 | 4.25 | 6.81 | 7.75 | 8.90 | 8.72 | 9.46 |
| 94 | Control (30 g sugar) | 5.0 | 0.04 | 0.59 | 4.49 | 5.29 | 6.19 | 8.60 | 5.81 | 5.72 |
| 95 | Control (No sugar) | 5.0 | 0.04 | 0.01 | 0.00 | 0.00 | 0.00 | 0.00 | 0.00 | 0.00 |
| 96 | No | 4.5 | 0.03 | 0.28 | 2.07 | 3.82 | 4.37 | 5.44 | 6.41 | 6.72 |
| 97 | Sample, | 5.0 | 0.04 | 0.27 | 2.63 | 4.15 | 7.42 | 8.16 | 8.63 | 9.13 |
| 98 | Xylose | 5.5 | 0.04 | 0.34 | 2.94 | 5.00 | 5.96 | 7.96 | 8.77 | 9.39 |
| 99 | only broth | 6.0 | 0.04 | 0.29 | 2.27 | 5.05 | 6.29 | 7.33 | 8.27 | 8.36 |
| 100 | | 6.5 | 0.04 | 0.28 | 1.59 | 4.40 | 5.72 | 5.61 | 6.93 | 6.21 |
| 101 | No | 4.5 | 0.02 | 0.18 | 1.50 | 2.13 | 1.91 | 2.37 | 1.99 | 0.23 |
| 102 | Sample, | 5.0 | 0.04 | 0.13 | 1.62 | 2.72 | 2.76 | 2.36 | 2.45 | 1.45 |
| 103 | Xylose | 5.5 | 0.04 | 0.12 | 0.99 | 2.31 | 1.62 | 1.52 | 1.41 | 0.06 |
| 104 | only | 6.0 | 0.04 | 0.09 | 0.87 | 1.77 | 1.90 | 2.03 | 1.66 | 0.09 |
| 105 | Broth | 6.5 | 0.04 | 0.13 | 1.17 | 2.54 | 2.66 | 2.69 | 2.08 | 0.89 |

Legend:
"CG" = Cut Grass;
"FG" = Freeze Ground;
0.xE = irradiated with 0.x MRads radiation using e-beam.

As indicated by the data in Table 1, the yield of ethanol generally increased with increasing dose or radiation, up to 90 MRad, after which yield leveled off at increasing doses. For a given dose of radiation and pH, the yield was generally significantly higher when the grass had also been freeze ground. For grass that had not been irradiated, or had received only low dose radiation, yields were markedly higher if the grass had been freeze ground.

OTHER EMBODIMENTS

The cooling and processing methods disclosed herein can also be used to treat other types of materials such as hydrocarbon-containing materials (e.g., petroleum-containing materials). Various types of petroleum-containing materials—including heavy and light crude oils, natural gas, oil sands, oil shale, tar sands, bitumen, coal, and/or various hydrocarbon blends—can be cooled and processed using the methods disclosed herein to promote separation of various components of the material, and to regulate temperature during refining, conversion, and purification processes such as cracking, reformation (catalytic and non-catalytic), distillation, and catalytic conversion, to improve the efficiency and to reduce the cost of such processes.

In some embodiments, the methods disclosed herein can be used to extract and/or separate hydrocarbon-containing materials from materials such as oil sands, oil shale, and tar sands. The methods can be used, for example, to separate petroleum-containing materials from sand, rock, and other inorganic and organic matter.

In the following sections, various petroleum processing steps are discussed; in general, cooling alone, or in combination with any of the processing techniques disclosed herein, can be used to improve the efficiency of these various processing steps.

Crude oils typically include large numbers of different hydrocarbon species, ranging from relatively light, volatile, low molecular weight hydrocarbons, to heavy, dense, highly viscous fractions (e.g., heavy oil, bitumen) of high molecular weight. The heavy crudes typically contain more sulfur and/or nitrogen and/or metals, relative to lighter, sweeter crudes such as the West Texas Intermediate, which is traded on the New York Mercantile Exchange. In general, sweet crudes include relatively low amounts of sulfur-containing compounds; the sour crudes include larger amounts of sulfur-containing compounds. Simple refineries are generally designed to handle sweet crudes, while more complex deep conversion refineries are required for the processing of heavy, sour crude oils.

The large number of different hydrocarbon (and other) species in crude oil typically establish a relatively delicately balanced colloidal solubility system. When certain properties of the crude oil are changed (e.g., temperature, pressure, and/or composition), the solubility balance can be destabilized, causing a single-phase crude oil feedstock to change to a multiphase, multicomponent mixture (which can include one or more gas, liquid, and solid phases). At room temperature and pressure, various components of crude oil are in different physical states. For example, lighter hydrocarbons (e.g., methane, ethane, propane, butane) are gases at room temperature and pressure. Components of intermediate molecular weight (e.g., pentane, hexane, octane, gasoline, kerosene, and diesel fuel) are liquids under these conditions. Heavy fractions (e.g., asphalt, wax) are solids at standard temperature and pressure. Due to this range of physical states, conventional refineries typically process crude oil at elevated temperatures and/or pressures to ensure that most (or all) of the hydrocarbon fractions in the crude are either liquids or gases Crude oil refining comprises processes that separate various hydrocarbon and other components in the oil and, in some cases, convert certain hydrocarbons to other hydrocarbon species via molecular rearrangement (e.g., chemical reactions that break bonds). In some embodiments, a first step in the refining process is a water washing step to remove soluble components such as salts from the crude oil. Typically, the washed crude oil is then directed to a furnace for preheating. As discussed above, the crude oil can include a large number of different components with different viscosities; some components may even be solid at room temperature. By heating the crude oil, the component mixture can be converted to a mixture that can be flowed from one processing system to another (and from one end of a processing system to the other) during refining.

Preheated crude is then sent to a distillation tower, where fractionation of various components in the crude oil mixture occurs with heating in a distillation column. The amount of heat energy supplied to the crude oil mixture in the distillation process depends in part upon the composition of the oil; in general, however, significant energy is expended in heating the crude oil during distillation, cooling the distillates, pressurizing the distillation column, and in other such steps. Within limits, certain refineries are capable of reconfiguration to handle differing crude oil feedstocks and products. In general, however, due to the relatively specialized refining apparatus, the ability of refineries to handle significantly different crude oil feedstocks is restricted.

In some embodiments, pretreatment of crude oil feedstocks using methods disclosed herein—including one or more cooling steps—can enhance the ability of a refining apparatus to accept crude oils having different compositions. For example, various chemical and/or physical properties of the crude oil mixture can be changed: lighter molecular weight components with lower viscosities can be produced from heavier components with higher viscosities; and certain components can be isomerized. The newly formed isomers can have lower viscosities than the components from which they are formed. The lighter molecular weight components and/or isomers with lower viscosities can then be introduced into the refinery, enabling processing of crude oil feedstock while may not have been suitable for processing initially.

In general, the various components of crude oil distill at different temperature ranges, corresponding to different vertical heights in a distillation column. Typically, for example, a refinery distillation column will include product streams at a large number of different temperature cut ranges, with the lowest boiling point (and, generally, smallest molecular weight) components drawn from the top of the column, and the highest boiling point, heaviest molecular weight components drawn from lower levels of the column. As an example, light distillates extracted from upper regions of the column typically include one or more of aviation gasoline, motor gasoline, napthas, kerosene, and refined oils. Intermediate distillates, removed from the middle region of the column, can include one or more of gas oil, heavy furnace oil, and diesel fuel oil. Heavy distillates, which are generally extracted from lower levels of the column, can include one or more of lubricating oil, grease, heavy oils, wax, and cracking stock. Residues remaining in the still can include a variety of high boiling components such as lubricating oil, fuel oil, petroleum jelly, road oils, asphalt, and petroleum coke. Certain other products can also be extracted from the column, including natural gas (which can be further refined and/or processed to produce components such as heating fuel, natural gasoline, liquefied petroleum gas, carbon black, and other petrochemicals), and various by-products (including, for example, fertilizers, ammonia, and sulfuric acid).

Generally, treatment of crude oil and/or components thereof using the methods disclosed herein can be used to modify molecular weights, chemical structures, viscosities, solubilities, densities, vapor pressures, and other physical properties of the treated materials. In general, a large number of different processing protocols can be implemented, according to the composition and physical properties of the feedstock.

Prior to and/or following distillation in a refinery, crude oil and/or components thereof can undergo a variety of other refinery processes to purify components and/or convert components into other products.

(i) Catalytic Cracking

Catalytic cracking is a widely used refinery process in which heavy oils are exposed to heat and pressure in the presence of a catalyst to promote cracking (e.g., conversion to lower molecular weight products). Originally, cracking was accomplished thermally, but catalytic cracking has largely replaced thermal cracking due to the higher yield of gasoline (with higher octane) and lower yield of heavy fuel oil and light gases. Most catalytic cracking processes can be classified as either moving-bed or fluidized bed processes, with fluidized bed processes being more prevalent. Process flow is generally as follows. A hot oil feedstock is contacted with the catalyst in either a feed riser line or the reactor. During the cracking reaction, the formation of coke on the surface of the catalyst progressively deactivates the catalyst. The catalyst and hydrocarbon vapors undergo mechanical separation, and oil remaining on the catalyst is removed by steam stripping. The catalyst then enters a regenerator, where it is reactivated by carefully burning off coke deposits in air. The hydrocarbon vapors are directed to a fractionation tower for separation into product streams at particular boiling ranges.

Older cracking units (e.g., 1965 and before) were typically designed with a discrete dense-phase fluidized catalyst bed in the reactor vessel, and operated so that most cracking occurred in the reactor bed. The extent of cracking was controlled by varying reactor bed depth (e.g., time) and temperature. The adoption of more reactive zeolite catalysts led to improved modern reactor designs in which the reactor is operated as a separator to separate the catalyst and the hydrocarbon vapors, and the cracking process is controlled by accelerating the regenerated catalyst to a particular velocity in a riser-reactor before introducing it into the riser and injecting the feedstock into the riser.

The methods disclosed herein can be used before, during, and/or after catalytic cracking to treat components of crude oil. In particular, the methods disclosed herein can be used to pre-treat feedstock prior to injection into the riser, to treat hydrocarbons (including hydrocarbon vapors) during cracking, and/or to treat the products of the catalytic cracking process.

Cracking catalysts typically include materials such as acid-treated natural aluminosilicates, amorphous synthetic silica-alumina combinations, and crystalline synthetic silica-alumina catalysts (e.g., zeolites). During the catalytic cracking process, components of crude oil can be exposed to ions from one or more ion beams to increase the efficiency of these catalysts. For example, the crude oil components can be exposed to one or more different types of metal ions that improve catalyst activity by participating in catalytic reactions. Alternatively, or in addition, the crude oil components can be exposed to ions that scavenge typical catalyst poisons such as nitrogen compounds, iron, nickel, vanadium, and copper, to ensure that catalyst efficiency remains high. Moreover, the ions can react with coke that forms on catalyst surfaces to remove the coke (e.g., by processes such as sputtering, and/or via chemical reactions), either during cracking or catalyst regeneration.

(ii) Alkylation

In petroleum terminology, alkylation refers to the reaction of low molecular weight olefins with an isoparaffin (e.g., isobutane) to form higher molecular weight isoparaffins. Alkylation can occur at high temperature and pressure without catalysts, but commercial implementations typically include low temperature alkylation in the presence of either a sulfuric acid or hydrofluoric acid catalyst. Sulfuric acid processes are generally more sensitive to temperature than hydrofluoric acid based processes, and care is used to minimize oxidation-reduction reactions that lead to the formation of tars and sulfur dioxide. In both processes, the volume of acid used is typically approximately equal to the liquid hydrocarbon charge, and the reaction vessel is pressurized to maintain the hydrocarbons and acid in a liquid state. Contact times are generally from about 10 to 40 minutes, with agitation to promote contact between the acid and hydrocarbon phases. If acid concentrations fall below about 88% by weight sulfuric acid or hydrofluoric acid, excessive polymerization can occur in the reaction products. The use of large volumes of strong acids makes alkylation processes expensive and potentially hazardous. The methods disclosed herein can be used before, during, and/or after alkylation to treat components of crude oil.

(iii) Catalytic Reforming and Isomerization

In catalytic reforming processes, hydrocarbon molecular structures are rearranged to form higher-octane aromatics for the production of gasoline; a relatively minor amount of cracking occurs. Catalytic reforming primarily increases the octane of motor gasoline.

Typical feedstocks to catalytic reformers are heavy straight-run naphthas and heavy hydrocracker naphthas, which include paraffins, olefins, naphthenes, and aromatics. Paraffins and naphthenes undergo two types of reactions during conversion to higher octane components: cyclization, and isomerization. Typically, paraffins are isomerized and converted, to some extent, to naphthenes. Naphthenes are subsequently converted to aromatics. Olefins are saturated to form paraffins, which then react as above. Aromatics remain essentially unchanged.

During reforming, the major reactions that lead to the formation of aromatics are dehydrogenation of naphthenes and dehydrocyclization of paraffins. The methods disclosed herein can be used before, during, and/or after catalytic reformation to treat components of crude oil. Catalysts used in catalytic reformation generally include platinum supported on an alumina base. Rhenium can be combined with platinum to form more stable catalysts that permit lower pressure operation of the reformation process. Without wishing to be bound by theory, it is believed that platinum serves as a catalytic site for hydrogenation and dehydrogenation reactions, and chlorinated alumina provides an acid site for isomerization, cyclization, and hydrocracking reactions. In general, catalyst activity is reduced by coke deposition and/or chloride loss from the alumina support. Restoration of catalyst activity can occur via high temperature oxidation of the deposited coke, followed by chlorination of the support.

(iv) Catalytic Hydrocracking

Catalytic hydrocracking, a counterpart process to ordinary catalytic cracking, is generally applied to crude oil components that are resistant to catalytic cracking A catalytic cracker typically receives as feedstock more easily cracked paraffinic atmospheric and vacuum gas oils as charge stocks. Hydrocrackers, in contrast, typically receive aromatic cycle oils and coker distillates as feedstock. The higher pressures and hydrogen atmosphere of hydrocrackers make these components relatively easy to crack.

In general, although many different simultaneous chemical reactions occur in a catalytic hydrocracker, the overall chemical mechanism is that of catalytic cracking with hydrogenation. In general, the hydrogenation reaction is exothermic and provides heat to the (typically) endothermic cracking reactions; excess heat is absorbed by cold hydrogen gas injected into the hydrocracker. Hydrocracking reactions are typically carried out at temperatures between 550 and 750° F., and at pressures of between 8275 and 15,200 kPa. Circulation of large quantities of hydrogen with the feedstock helps to reduce catalyst fouling and regeneration. Feedstock is typically hydrotreated to remove sulfur, nitrogen compounds, and metals before entering the first hydrocracking stage; each of these materials can act as poisons to the hydrocracking catalyst.

Most hydrocracking catalysts include a crystalline mixture of silica-alumina with a small, relatively uniformly distributed amount of one or more rare earth metals (e.g., platinum, palladium, tungsten, and nickel) contained within the crystalline lattice. Without wishing to be bound by theory, it is believed that the silica-alumina portion of the catalyst provides cracking activity, and the rare earth metals promote hydrogenation. Reaction temperatures are generally raised as catalyst activity decreases during hydrocracking to maintain the reaction rate and product conversion rate. Regeneration of the catalyst is generally accomplished by burning off deposits which accumulate on the catalyst surface. The methods disclosed herein can be used before, during, and/or after catalytic hydrocracking to treat components of crude oil.

(v) Other Processes

A variety of other processes that occur during the course of crude oil refining can also be improved by, or supplanted by, the methods disclosed herein. For example, the methods disclosed herein can be used before, during, and/or after refinery processes such as coking, thermal treatments (including thermal cracking), hydroprocessing, and polymerization to improve the efficiency and overall yields, and reduce the waste generated from such processes.

For example, the methods and systems disclosed herein can be used to make a variety of different products, or intermediate products that can be further processed into other products. For example, any of the disclosed mechanical processing methods can be used to make resin fiber composites that include resins such as polyethylene, polypropylene, and/or lignin.

A number of embodiments have been described. Nevertheless, it will be understood that various modifications may be made without departing from the spirit and scope of the invention. Accordingly, other embodiments are within the scope of the claims.

What is claimed is:

1. A method comprising:
   comminuting a lignocellulosic biomass material;
   cooling the comminuted biomass material to 280° K (6.85° C.) or less;
   after cooling, comminuting the cooled biomass material;
   either before or after cooling, irradiating the biomass material;
   after the second comminuting step, contacting the material with an enzyme and/or a microorganism to release sugars; and
   fermenting the released sugars.

2. The method of claim 1, wherein the biomass material is irradiated after cooling.

3. The method of claim 1, wherein the biomass material is irradiated prior to cooling.

4. The method of claim 1 wherein cooling is performed in a freeze grinding or freeze milling device.

5. The method of claim 1 wherein fermenting is performed under conditions selected to produce an alcohol.

6. The method of claim 5 wherein the alcohol comprises ethanol or n-butanol.

7. The method of claim 1 wherein cooling comprises cooling the material to a temperature below the brittle point of the material.

8. The method of claim 2, further comprising cooling again after irradiating.

9. The method of claim 1 wherein cooling comprises temperature cycling the starting material.

10. The method of claim 1 wherein the biomass material has a bulk density of less than 0.3 g/cm$^3$.

11. The method of claim 1, wherein irradiating is performed using an electron beam.

12. The method of claim 11, wherein the biomass material receives a dose of radiation of from about 10 MRad to 100 MRad.

13. The method of claim 11, wherein the biomass material receives a dose of radiation of from about 30 MRad to 90 MRad.

14. The method of claim 1 wherein the biomass material is selected from the group consisting of wood, grasses, rice hulls, bagasse, jute, hemp, flax, bamboo, sisal, abaca, straw, corn cobs, coconut hair, algae, seaweed, and mixtures of any of these.

15. The method of claim 1 wherein the biomass material has a bulk density of less than 0.8 g/cm$^3$.

* * * * *

UNITED STATES PATENT AND TRADEMARK OFFICE
CERTIFICATE OF CORRECTION

PATENT NO. : 8,418,944 B2
APPLICATION NO. : 12/859003
DATED : April 16, 2013
INVENTOR(S) : Marshall Medoff It is certified that error appears in the above-identified patent and that said Letters Patent is hereby corrected as shown below:

On the Title Page, Item (73) Assignee: Please replace "Xylero, Inc., Woburn, MA (US)" with "Xyleco, Inc., Woburn, MA (US)"

Signed and Sealed this
Twenty-eighth Day of May, 2013

Teresa Stanek Rea
*Acting Director of the United States Patent and Trademark Office*